United States Patent
Gutman

[11] B 3,995,032
[45] Nov. 30, 1976

[54] INSECTICIDAL AND MITICIDAL METHOD CONTAINING PHOSPHORUS COMPOUNDS

[75] Inventor: Arnold G. Gutman, Berkley, Calif.

[73] Assignee: Stauffer Chemical Company, Westport, Conn.

[22] Filed: May 12, 1975

[21] Appl. No.: 576,903

[44] Published under the second Trial Voluntary Protest Program on February 3, 1976 as document No. B 576,903.

Related U.S. Application Data

[60] Continuation-in-part of Ser. No. 353,868, April 23, 1973, abandoned, which is a division of Ser. No. 123,410, March 11, 1971, Pat. No. 3,780,143.

[52] U.S. Cl............................. 424/203; 424/210; 424/216; 424/217; 424/218; 424/219; 424/222

[51] Int. Cl.²......................................... A01N 9/36

[58] Field of Search................ 424/203, 340.5, 210, 424/216, 217, 222, 218, 219

[56] References Cited
UNITED STATES PATENTS

| | | | |
|---|---|---|---|
| 3,060,087 | 10/1962 | Kingsbury et al. | 424/203 |
| 3,094,406 | 6/1963 | Price et al. | 424/203 |

Primary Examiner—Dale R. Ore
Attorney, Agent, or Firm—Daniel C. Block

[57] ABSTRACT

A method of controlling insects and mites comprising applying to the habitat infested with mites and insects an effective insecticidal and midicidal amount of a compound of the generic formula:

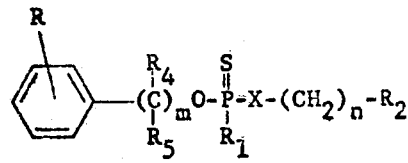

wherein R can be selected from the group consisting of hydrogen, nitro, halogen, alkoxy, alkyl and methylenedioxy; $R_1$ can be selected from alkyl and alkoxy; X can be sulfur or oxygen, $n$ is zero or one and $R_2$ can be selected from hydrogen, thioalkyl, cyano, thioalkylaryl, alkynyl, and a mono or multisubstituted group represented by

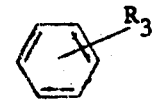

wherein $R_3$ can be selected from hydrogen, alkyl, thioalkyl, nitro, halogen, cyano and mixtures thereof; $R_4$ can be hydrogen or alkyl; $R_5$ can be hydrogen or alkyl; $m$ is a whole number ranging between 1 and 4; provided that when $n$ is zero then $R_2$ is

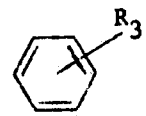

The compounds are useful as insecticides and miticides.

6 Claims, No Drawings

INSECTICIDAL AND MITICIDAL METHOD CONTAINING PHOSPHORUS COMPOUNDS

CROSS-REFERENCE TO RELATED APPLICATION

This application is a continuation-in-part of application Ser. No. 353,868 filed Apr. 23, 1973 now abandoned, which is a divisional of application Ser. No. 123,410 filed Mar. 11, 1971, now U.S. Pat. No. 3,780,143.

DESCRIPTION OF THE INVENTION

This invention is directed to a method of using a novel group of compounds which may be generally described as phosphorus derivatives which are active insecticides and miticides. The compounds of the present invention are represented by the generic formula:

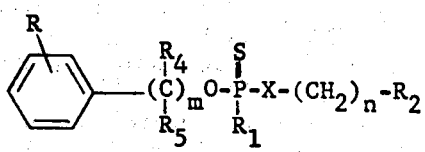

wherein R can be selected from the group consisting of hydrogen, nitro, halogen, alkoxy, alkyl and methylenedioxy; $R_1$ can be selected from alkyl and alkoxy; X can be sulfur or oxygen, $n$ is zero or one and $R_2$ can be selected from hydrogen, thioalkyl, cyano, thioalkylaryl, alkynyl, and a mono or multisubstituted group represented by

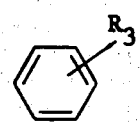

wherein $R_3$ can be selected from hydrogen, alkyl, thioalkyl, nitro, halogen, cyano and mixtures thereof; $R_4$ can be hydrogen or alkyl; $R_5$ can be hydrogen or alkyl; $m$ is a whole number ranging between 1 and 4; provided that when $n$ is zero then $R_2$ is

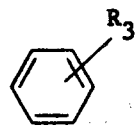

As a specific embodiment, R is methylenedioxy, $R_1$ is ethyl, X is sulfur, $n$ is 1, $m$ is 1, $R_2$ is selected from a group consisting of hydrogen, methylthio, ethynyl, cyano, and benzylthio; $R_4$ and $R_5$ are hydrogen.

In general, the above-noted compounds can be prepared by reacting an appropriate alcohol with ethylthiophosphine sulfide to form a reactive mercaptan. The mercaptan is then treated with a halide compound in the presence of a base such as triethylamine to form the end product. In the alternative, the mercaptan can be reacted with a chlorinating agent, such as sulfuryl chloride, to form the chloridate which can be further reacted with an appropriate compound in the presence of a base to form the end product. Another method involves the reaction of an appropriate alcohol with a dihalothiophosphorous derivative to obtain a reactive thiochloridate phosphorous intermediate which is reacted with an appropriate compound to form the end product.

In order to illustrate the merits of the present invention, the following examples are provided.

EXAMPLE 1

0-(4-nitrobenzyl), ethyl-S-(propargyl)phosphonodithioate

To a 1 liter flask was added 200 ml. of dioxane and 6.2 g. (0.025 moles) ethylthionophosphine sulfide. The mixture was stirred at room temperature and then 7.65 g. (0.05 moles) of 4-nitrobenzyl alcohol was added. The temperature rose to 30°C. and the solution became clear. The resulting solution was stirred at 30°C. for 30 minutes, cooled in an ice bath to 10°. Then, 5.95 g. (0.05 moles) of propargylbromide was added at once and/or along with 10.1 g. of triethylamine was added over a period of 10 minutes and at such a rate that the temperature did not exceed 20°C. The mixture was stirred at room temperature for 1 hour, poured into 500 ml. of benzene, washed with 200 ml. of water, 100 ml. of saturated sodium bicarbonate, twice with 100 ml. of water and dried over magnesium sulfate and evaporated. The yield was 11.1 g. having $n_D^{30}$ — 1.5745.

EXAMPLE 2

0-(2-methoxybenzyl), ethyl-S-methylphosphonodithioate

To a 1 liter flask was added 12.4 g. (0.05 moles) of ethylthionophosphine sulfide and 200 ml. of dioxane. The mixture was stirred at room temperature and then 13.8 g. (0.1 mole) of 2-methoxybenzyl alcohol was added. The temperature rose to 30°C. and the solution became clear. The resulting solution was stirred at 30° for 30 minutes, then cooled in an ice bath to 10°. Then, 14.2 g. (0.01 mole) of methyl iodide was added at once and then 15.1 g. (0.15 mole) of triethylamine was added over a period of 10 minutes, and at such a rate that the temperature did not exceed 20°C. The mixture was stirred at room temperature for 1 hour, poured into 500 ml. of benzene, washed with 200 ml. of water, 100 ml. of saturated sodium bicarbonate, and twice with 100 ml. of water, dried over magnesium sulfate and evaporated to yield 21 g. of product, $n_D^{30}$ — 1.5677.

EXAMPLE 3

0-benzyl-0-ethyl phosphorothiochloridate 54 o. (0.5 mole) of benzyl alcohol, 56 g. (0.5 mole) of potassium t-butoxide and 500 ml. of tetrahydrofuran was combined and heated under reflux for 1 hour. The resulting solution was cooled to room temperature and was added over a period of 1 hour to a stirring solution of 89.5 g. (0.5 mole) of ethyl dichlorothiophosphate. The reaction temperature during the addition was maintained at −10° to −5°. After the addition was complete, the mixture was allowed to warm to room temperature and was stirred for 1 hour. The mixture was then poured into 500 ml. of benzene and was washed with three 300 ml. portions of water. The benzene phase was dried with anhydrous $MgSO_4$ and evaporated under reduced pressure to yield 101 g. of the desired product, $n_D^{30}$ — 1.5347.

EXAMPLE 4

O-benzyl-O-(4-cyanophenol),ethyl phosphorodithioate 4.75 o. (0.04 mole) of 4-cyanophenol was combined with 1.6 g. (0.04 mole) of caustic and 20 ml. of water in a 500 ml. three-neck flask fitted with a stirrer, thermometer, and dropping funnel. The mixture was stirred and 10.0 g. (0.04 mole) of the product of Example 3 in 200 ml. of tetrahydrofuran was added over a period of 30 minutes. The resulting mixture was stirred and heated under reflux for 2 hours, cooled and poured into 400 ml. of benzene. The benzene mixture was washed with 200 ml. of water, 200 ml. of dilute caustic solution, followed by two 200 ml. portions of water. The benzene phase was dried with anhydrous MgSO$_4$ and evaporated under reduced pressure to yield 10.0 g. (86.7% theory) of product, $n_D^{30}$ — 1.5477.

EXAMPLE 5

O-benzyl,ethyl phosphonothiochloridate 108 o. (1.0 mole) of benzyl alcohol, 124 g. (0.5 mole) of ethylthionophosphine sulfide was combined with 400 ml. of benzene in a one l. three-neck flask fitted with a stirrer, thermometer, condenser and dropping funnel. The mixture was stirred at 40°–50°C. for 1 hour until a clear solution was obtained. The temperature was maintained at 40°–50° and 135 g. (1.0 mole) of sulfuryl chloride was added over a period of 30 minutes. After the addition was complete, the mixture was stirred at 40°–50° for an additional 30 minutes. The solvent was removed under aspirator pressure and the residue distilled in vacuo to yield 101 g., b.p. 114–120/100 μ.

EXAMPLE 6

O-benzyl-S-(4-chlorophenyl),ethyl phosphonodithioate 6.2 o. (0.042 mole) of 4-chlorothiophenol was combined with 1.7 g. (0.042 mole) of caustic and 20 ml. of water in a 500 ml. three-neck flask fitted with a stirrer, thermometer, and dropping funnel. The mixture was stirred and 10.0 g. (0.042 mole) of the product of Example 5 in 200 ml. of tetrahydrofuran was added over a period of 30 minutes. The resulting mixture was stirred and heated under reflux for 2 hours, cooled and poured into 400 ml. of benzene. The benzene mixture was washed with 200 ml. of water, 200 ml. of dilute caustic solution, followed by two 200 ml. portions of water. The benzene phase was dried with anhydrous MgSO$_4$ and evaporated under reduced pressure to yield 11.0 g. of product, $n_D^{30}$ — 1.6182.

EXAMPLE 7

O-(piperonyl)ethyl-S-(methylthiomethyl)phosphonodithioate

To a 1-liter flask was added 200 ml. of dioxane and 12.4 g. (0.05 mole) ethylthionophosphine sulfide. The mixture was stirred at room temperature and then 15.2 g. (0.10 mole) of piperonyl alcohol was added. The temperature rose to 30°C. and the solution became clear. The resulting solution was stirred at 30°C. for 30 minutes, cooled in an ice bath to 10°C. Then, 9.7 g. (0.1 mole) of chloromethyl,methylsulfide was added at once and/or along with 15.1 g. of triethylamine was added over a period of 10 minutes and at such a rate that the temperature did not exceed 20°C. The mixture was stirred at room temperature for 1 hour, poured into 500 ml. of benzene, washed with 200 ml. of water, 100 ml. of saturated sodium bicarbonate, twice with 100 ml. of water and dried over magnesium sulfate and evaporated. The yield was 23.0 g. having $n_D^{30}$ — 1.5942.

Other compounds were prepared in an analogous manner starting with the appropriate materials as outlined above. The following is a table of compounds representative of those embodied by the present invention. Compound numbers have been assigned to them and are used for identification throughout the balance of the specification.

TABLE I

| Compound No. | m | n | X | R | R$_1$ | R$_2$ | R$_3$ | R$_4$ | R$_5$ |
|---|---|---|---|---|---|---|---|---|---|
| 1 | 1 | 1 | S | 4-NO$_2$ | C$_2$H$_5$ | C≡CH | — | H | H |
| 2 | 1 | 1 | S | 4-NO$_2$ | C$_2$H$_5$ | SC$_2$H$_5$ | — | H | H |
| 3 | 1 | 1 | S | 4-Cl | C$_2$H$_5$ | C≡CH | — | H | H |
| 4 | 1 | 1 | S | 4-Cl | C$_2$H$_5$ | CN | — | H | H |
| 5 | 1 | 1 | S | 4-Cl | C$_2$H$_5$ | SC$_2$H$_5$ | — | H | H |
| 6 | 1 | 1 | S | H | C$_2$H$_5$ | CN | — | H | H |
| 7 | 1 | 1 | S | H | C$_2$H$_5$ | H | — | H | H |
| 8 | 1 | 1 | S | H | C$_2$H$_5$ | C≡CH | — | H | H |
| 9 | 1 | 1 | S | H | C$_2$H$_5$ | SCH$_2$–⟨phenyl⟩ | — | H | H |
| 10 | 1 | 1 | S | 2-OCH$_3$ | C$_2$H$_5$ | H | — | H | H |
| 11 | 1 | 1 | S | 2-OCH$_3$ | C$_2$H$_5$ | C≡CH | — | H | H |
| 12 | 1 | 1 | S | 2-OCH$_3$ | C$_2$H$_5$ | SC$_2$H$_5$ | — | H | H |
| 13 | 1 | 1 | S | 4-i-C$_3$H$_7$ | C$_2$H$_5$ | SCH$_2$–⟨phenyl⟩ | — | H | H |
| 14 | 1 | 1 | S | CH$_2$(3,4-O–,O–) | C$_2$H$_5$ | H | — | H | H |

TABLE I-continued $$\underset{R_5}{\overset{R_4}{\underset{|}{(C)_m}}}\text{—O—}\underset{R_1}{\overset{S}{\underset{\|}{P}}}\text{—X—}(CH_2)_n\text{—}R_2$$

with R on phenyl ring

| Compound No. | m | n | X | R | $R_1$ | $R_2$ | $R_3$ | $R_4$ | $R_5$ |
|---|---|---|---|---|---|---|---|---|---|
| 15 | 1 | 1 | S | CH₂- with 3,4-O—/O— | $C_2H_5$ | $SCH_3$ | — | H | H |
| 16 | 1 | 1 | S | CH₂- with 3,4-O—/O— | $C_2H_5$ | C≡CH | — | H | H |
| 17 | 1 | 1 | S | CH₂- with 3,4-O—/O— | $C_2H_5$ | C≡N | — | H | H |
| 18 | 1 | 1 | S | CH₂- with 3,4-O—/O— | $C_2H_5$ | SCH₂-phenyl | — | H | H |
| 19 | 1 | 0 | S | H | $C_2H_5$ | phenyl | 4-Cl | H | H |
| 20 | 1 | 0 | S | H | $C_2H_5$ | phenyl | 4-CH₃ | H | H |
| 21 | 1 | 0 | O | H | $C_2H_5$ | phenyl | 4-NO₂ | H | H |
| 22 | 1 | 0 | O | H | $C_2H_5$ | phenyl | 3-CH₃, 4-NO₂ | H | H |
| 23 | 1 | 0 | S | H | $OC_2H_5$ | phenyl | 4-Cl | H | H |
| 24 | 1 | 0 | S | H | $OC_2H_5$ | phenyl | H | H | H |
| 25 | 1 | 0 | O | H | $C_2H_5$ | phenyl | 3-C≡N | H | H |
| 26 | 1 | 0 | O | H | $OC_2H_5$ | phenyl | 3-C≡N | H | H |
| 27 | 1 | 0 | O | H | $OC_2H_5$ | phenyl | 2,4,5-Cl | H | H |
| 28 | 1 | 0 | O | H | $OC_2H_5$ | phenyl | 3-CH₃, 4-NO₂ | H | H |
| 29 | 1 | 0 | O | H | $OC_2H_5$ | phenyl | 4-NO₂ | H | H |
| 30 | 1 | 0 | O | H | $OC_2H_5$ | phenyl | 3-CF₃ | H | H |
| 31 | 1 | 0 | S | H | $OC_2H_5$ | phenyl | 3-CH₃ | H | H |

TABLE I-continued $$\text{(structure)} \quad \underset{R_5}{\overset{R}{\diagdown}}\hspace{-2pt}\underset{}{\overset{}{\diagup}}\hspace{-2pt}\text{—}(\overset{R_4}{\underset{R_5}{C}})_m O - \overset{S}{\underset{R_1}{P}} - X - (CH_2)_n - R_2$$

| Compound No. | m | n | X | R | $R_1$ | $R_2$ | $R_3$ | $R_4$ | $R_5$ |
|---|---|---|---|---|---|---|---|---|---|
| 32 | 1 | 1 | S | H | $C_2H_5$ | C≡CH | — | H | $CH_3$ |
| 33 | 1 | 1 | S | H | $C_2H_5$ | C≡N | — | H | $CH_3$ |
| 34 | 1 | 1 | S | H | $C_2H_5$ | $SCH_3$ | — | H | $CH_3$ |
| 35 | 2 | 1 | S | H | $C_2H_5$ | C≡N | — | H | H |
| 36 | 2 | 1 | S | H | $C_2H_5$ | C≡CH | — | H | H |
| 37 | 1 | 1 | S | H | $C_2H_5$ | phenyl | H | H | H |
| 38 | 1 | 1 | O | H | $C_2H_5$ | phenyl | 2,4,5-Cl | H | H |
| 39 | 1 | 1 | O | H | $C_2H_5$ | phenyl | 4-Cl | H | H |
| 40 | 1 | 1 | O | H | $C_2H_5$ | phenyl | 4-$SCH_3$ | H | H |

Entomological Testing Methods

I. House fly [*Musca domestica* (L.)]

A stock solution containing 100 μg/ml of the toxicant in an appropriate solvent is prepared. Aliquots of this solution are combined with 1 ml of an acetone-peanut oil solution in a dish, 55 mm. in diameter, and allowed to dry. The aliquots are varied to achieve desired toxicant concentrations ranging from 100 μg per dish to that at which 50% mortality is obtained. The dishes are placed in a circular cardboard cage, closed on the bottom with cellophane and covered on top with cloth netting. Twenty-five female house flies are introduced into the cage and the percent mortality is recorded after 48 hours. LD-50 values are expressed in terms of μg per 25 female flies.

II. German Cockroach [*Blattela germanica* (Linne)]

Ten 1-month old nymphs are placed into a circular cardboard cage sealed on one end with cellophane and covered by cloth netting on the other. Aliquots of the toxicant, dissolved in an appropriate solvent, are diluted in water to which has been added 0.0002% of a conventional wetting agent such as polyoxy-ethylene sorbitan monolaurate ether of alkylated phenols blended with organic sulfonates. Test concentrations range from 0.1% to that at which 50% mortality is obtained. Each of these aqueous suspensions are sprayed onto the insects, through the cloth netting, by means of a hand spray gun.

III. Lygus Bug [*Lygus hesperus* (Knight)]

Same as for the German cockroach except that the test concentrations range from 0.05% to that at which 50% mortality is obtained.

IV. Salt-marsh Caterpillar [*Estigmene acrea* (Drury)]

Test solutions are prepared in an identical manner and concentrations are the same as those for the German cockroach (II). Sections of bitter dock (*Rumex obtusifolius*) leaves, 1–1.5 inches in length are immersed in the test solutions for 10–15 seconds and placed on a wire screen to dry. The dried leaf is placed on a moistened piece of filter paper in a petri dish and infested with five third-instar larvae. Mortality of the larvae is recorded after 72 hours and the LD-50 values are expressed as percent active ingredient in the aqueous suspensions.

V. Beet Armyworm [*Spodoptera exigua* (Hubner)]

Same as salt-marsh caterpillar (IV) except that leaves of Romaine lettuce (*Latuca sativa*) are used as the host plant.

VI. Tobacco Budworm [*Heliothis virescens* (F.)]

Same as for Beet Armyworm.

VII. Black Bean Aphid [*Aphis fabae* (Scop.)]

Nasturtium (*Tropaeolum* sp.) plants, approximately 2–3 inches tall, are transplanted into sandy loam soil in 3 inch clay pots and infested with 50–75 aphids of mixed ages. Twenty-four hours later they are sprayed, to the point of runoff, with aqueous suspensions of the toxicant. The suspensions are prepared as in previously described tests. Test concentrations ranged from 0.05% to that at which 50% mortality is obtained. Mortality is recorded after 48 hours and the LD-50 values are expressed as percent active ingredient in the aqueous suspensions.

VIII. Two-spotted Mite [*Tetranychus urticae* (Koch)]

Same as for the black bean aphid except that pinto beans (*Phaseolus* sp.) are utilized as the host plant rather than nasturtiums.

IX. Systemic Tests

A. Black bean aphid

Aliquots of the toxicant dissolved in an appropriate solvent are incorporated into 1 pound samples of sandy loam soil and placed into 1 pint ice-cream cartons. Test concentrations range from 10 ppm of toxicant per pound of soil down to that at which 50% mortality is obtained. Nasturtium (*Tropaeolum* sp.) plants approximately 2–3 inches tall are transplanted into the treated soil and infested with 50–75 aphids of various ages. Mortality is recorded 72 hours after infestation, and LD-50 values are expressed as ppm of active ingredient per pound of soil.

B. Two-spotted mite

Preparation of the test solution and concentrations is the same as for the salt-marsh caterpillar test. Pinto bean (*Phaseolus* sp.) plants with expanded primary leaves are placed in the solution so that the roots and major portions of the stem are completely immersed. Immediately after, the leaves are infested with 75–100 mites of various ages. Mortality of adults, nymphs and eggs is recorded after one week, and LD-50 values are expressed as ppm of toxicant in the aqueous suspensions.

wherein R is methylenedioxy; $R_1$ is ethyl; X is sulfur; $n$ and $m$ are one; $R_2$ is selected from hydrogen, methylthio, cyano, benzylthio, and ethynyl; and, $R_4$ and $R_5$ are hydrogen.

2. The method in accordance with claim 1 wherein

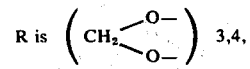

and $R_2$ is H.

3. The method in accordance with claim 1 wherein

TABLE II

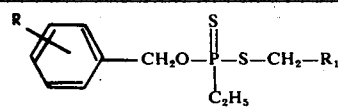

| Compound No. | HF μg | GR % | LB % | BA % | BAS ppm | SMC % | BAW % | TBW % | Two-Spotted Mite PE % | Eggs % | Sys ppm |
|---|---|---|---|---|---|---|---|---|---|---|---|
| 1 | 30 | >.1 | >.05 | .008 | >10 | >.1 | >.1 | >.1 | .005 | .008 | >10 |
| 2 | 30 | >.1 | .05 | .0005 | >10 | >.1 | .08 | >.1 | .001 | .003 | >10 |
| 3 | 10 | >.1 | .03 | .008 | >10 | >.1 | >.1 | .05 | .001 | .03 | >10 |
| 4 | 30 | .03 | .01 | .003 | >10 | >.1 | >.1 | .1 | .003 | .03 | >10 |
| 5 | 30 | .05 | .03 | .0008 | >10 | >.1 | >.1 | .1 | .003 | .03 | >10 |
| 6 | 30 | >.1 | .003 | .003 | 8 | .03 | .03 | .01 | .003 | .03 | >10 |
| 7 | 30 | .1 | .008 | .03 | >10 | .03 | >.1 | .05 | .05 | >.05 | >10 |
| 8 | 6 | .03 | .003 | .003 | >10 | .01 | .03 | .005 | .005 | .05 | >10 |
| 9 | 60 | >.1 | .05 | .001 | >10 | .1 | >.1 | .05 | .003 | .008 | >10 |
| 10 | 85 | >.1 | >.05 | .05 | >10 | >.1 | >.1 | >.1 | .05 | >.05 | >10 |
| 11 | 60 | >.1 | .03 | .005 | >10 | .1 | .08 | .08 | .03 | >.05 | >10 |
| 12 | 100 | >.1 | .01 | .003 | >10 | >.1 | >.1 | >.1 | .01 | .03 | >10 |
| 13 | >100 | | | >.05 | | >.1 | | | >.05 | >.05 | |
| 14 | 60 | >.1 | >.05 | >.05 | | >.1 | >.1 | >.1 | >.05 | >.05 | |
| 15 | 40 | >.1 | >.05 | .008 | >10 | >.1 | >.1 | .1 | .03 | >.05 | >10 |
| 16 | 35 | >.1 | .05 | .05 | >10 | >.1 | >.1 | >.1 | .01 | >.05 | >10 |
| 17 | >100 | | | >.05 | | >.1 | | | >.05 | >.05 | |
| 18 | >100 | >.1 | >.05 | >.05 | | >.1 | | | >.05 | >.05 | |
| 19 | 30 | >.1 | .05 | .005 | >10 | .1 | .08 | .01 | <.05 | <.05 | >10 |
| 20 | 30 | >.1 | >.05 | .003 | >10 | >.1 | | | <.05 | <.05 | >10 |
| 21 | 8 | .1 | .008 | .0003 | >10 | .03 | .05 | .03 | <.05 | >.05 | >10 |
| 22 | 25 | .05 | .008 | .0003 | >10 | .05 | >.1 | .08 | <.05 | <.05 | >10 |
| 23 | >100 | | | >.05 | | >.1 | | | >.05 | >.05 | |
| 24 | >100 | | | >.05 | | >.1 | | | >.05 | >.05 | |
| 25 | 8 | .03 | .005 | .0003 | >10 | .05 | >.1 | .03 | <.05 | <.05 | >10 |
| 26 | 30 | >.1 | | >.05 | | >.1 | >.1 | | .05 | <.05 | >10 |
| 27 | >100 | | | >.05 | | >.1 | | | <.05 | <.05 | >10 |
| 28 | 40 | | | >.05 | | >.1 | | | >.05 | <.05 | >10 |
| 29 | 30 | | | .008 | >10 | >.1 | | | >.05 | >.05 | |
| 30 | 100 | >.1 | >.05 | >.05 | | >.1 | | | >.05 | >.05 | |
| 31 | >100 | | | >.05 | | >.1 | | | >.05 | >.05 | |
| 32 | 15 | | | .03 | >10 | .1 | | | <.05 | <.05 | >10 |
| 33 | 30 | | | .003 | >10 | .03 | .05 | .08 | | | |
| 34 | 35 | .1 | | .0003 | >10 | >.1 | | | <.05 | <.05 | >10 |
| 35 | 25 | | | .008 | >10 | .05 | .01 | .05 | <.05 | <.05 | >10 |
| 36 | 8 | | | .01 | >10 | >.1 | | | <.05 | <.05 | >10 |
| 37 | 12 | .1 | .05 | .003 | >10 | .03 | .1 | .05 | <.05 | <.05 | >10 |
| 38 | 30 | >.1 | .05 | .0008 | >10 | >.1 | >.1 | | .05 | <.05 | >10 |
| 39 | 30 | >.1 | .05 | >.05 | | >.1 | .1 | | >.05 | <.05 | >10 |
| 40 | 7 | .03 | .001 | .0003 | | >.1 | | | <.05 | <.05 | >10 |

What is claimed is:

1. The method of controlling insects and mites comprising applying to the habitat infested with mites and insects an effective insecticidal and miticidal amount of a compound corresponding to the formula

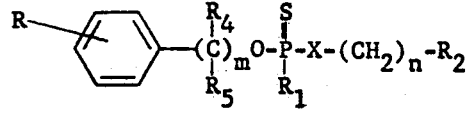

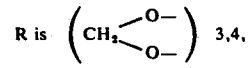

and $R_2$ is $SCH_3$.

4. The method in accordance with claim 1 wherein

R is  3,4;
$R_2$ is C≡CH.
5. The method in accordance with claim 1 wherein
R is (CH₂⟨O-/O-⟩)₃,₄,
and $R_2$ is C≡N.
6. The method in accordance with claim 1 wherein
R is  3,4,
and $R_2$ is $SCH_2$
SCH₂—⌬.
* * * * *